(12) United States Patent
Luo et al.

(10) Patent No.: US 12,130,218 B2
(45) Date of Patent: Oct. 29, 2024

(54) METHOD FOR CALCULATING SURFACE ENERGY MATCHING INDEX OF SPECIFIC SURFACE AREA OF ASPHALT MORTAR-AGGREGATE

(71) Applicant: WUHAN UNIVERSITY OF TECHNOLOGY, Wuhan (CN)

(72) Inventors: Rong Luo, Wuhan (CN); Yicheng Hu, Wuhan (CN); Tingting Huang, Wuhan (CN); Qiang Miao, Wuhan (CN); Yu Liang, Wuhan (CN)

(73) Assignee: WUHAN UNIVERSITY OF TECHNOLOGY, Wuhan (CN)

( * ) Notice: Subject to any disclaimer, the term of this patent is extended or adjusted under 35 U.S.C. 154(b) by 261 days.

(21) Appl. No.: 17/750,385

(22) Filed: May 22, 2022

(65) Prior Publication Data

US 2023/0175942 A1 Jun. 8, 2023

(30) Foreign Application Priority Data

Dec. 2, 2021 (CN) .......................... 202111473122.9

(51) Int. Cl.
*G01N 13/00* (2006.01)
*C04B 18/02* (2006.01)
*C04B 26/26* (2006.01)

(52) U.S. Cl.
CPC ............. *G01N 13/00* (2013.01); *C04B 18/02* (2013.01); *C04B 26/26* (2013.01)

(58) Field of Classification Search
CPC ......... G01L 5/14; G01L 23/00; G01L 5/0052; G01L 19/0092; G01L 19/0609; G01L 19/0636; G01L 19/0681; G01L 19/083
See application file for complete search history.

(56) References Cited

FOREIGN PATENT DOCUMENTS

| CN | 106930167 A | * | 7/2017 | ............... E01C 7/35 |
| CN | 106946501 A | * | 7/2017 | ............. C04B 26/26 |

* cited by examiner

*Primary Examiner* — Andre J Allen
(74) *Attorney, Agent, or Firm* — Jeenam Park

(57) ABSTRACT

Disclosed is a method for calculating surface energy matching index of specific surface area of asphalt mortar-aggregate, including the following steps: determining surface energy parameter of aggregate by vapor adsorption method; determining surface energy parameter of filler by improved capillary rising method; determining specific surface area of asphalt mixture aggregate by specific surface area coefficient method; using an automatic specific surface area and pore analyzer to determine the specific surface area of the filler; calculating adhesive bond energy of the asphalt mixture and adhesive bond energy under liquid condition; calculating the surface energy matching index of asphalt mortar-aggregate. The beneficial effects of this disclosure include: the water stability of asphalt mixture is improved because the influence of the surface energy matching index of the specific surface area of asphalt mortar-aggregate is considered.

8 Claims, 4 Drawing Sheets

METHOD FOR CALCULATING SURFACE ENERGY MATCHING INDEX OF SPECIFIC SURFACE AREA OF ASPHALT MORTAR-AGGREGATE

FIELD OF THE DISCLOSURE

The disclosure relates to the technical field of road engineering, in particular to a method for calculating surface energy matching index of specific surface area of asphalt mortar-aggregate.

BACKGROUND

Asphalt pavement is one of the main structures of highways and urban roads in China. During the design and construction of the asphalt mixture for its surface layer, it is necessary to focus on the adhesion performance of asphalt and aggregate, which is directly related to road performance such as the fatigue life length, self-healing ability and water stability of the asphalt mixture. Asphalt mixture is a composite material with rheological properties, which is composed of aggregates, asphalt, and fillers.

Studies have shown that the two main manifestations of cracking of asphalt pavement under the action of vehicle load, temperature stress, and water are: (1) cohesive cracking: cracking occurs inside the asphalt or asphalt mortar; (2) adhesion cracking: cracking occurs between the asphalt and aggregate interface. Due to the huge difference in apparent properties between fillers and coarse aggregates, the rules of cohesive cracking and adhesion cracking are different. Macroscopically, the cracking of the interface between asphalt and aggregate and the internal cracking of asphalt mortar are inconsistent. At the same time, the water damage resistance of asphalt mixture depends on the bond strength of asphalt mortar and aggregate composed of asphalt and filler. Therefore, it is of great significance to accurately evaluate the performance of asphalt mortar and determine the reasons for the different performance of cohesive cracking and adhesion cracking of asphalt mixtures, which is of great significance for in-depth research on the water damage resistance of asphalt mixtures and improving the service performance of asphalt mixtures.

There are many methods to test the adhesion performance of asphalt and aggregate in China, among which the most used in engineering is "T 0616-1993 asphalt and coarse aggregate adhesion test" method in the current specification of China's highway engineering asphalt and asphalt mixture test regulations" (JTG E20-2011). This method is divided into boiling method and water immersion method according to the particle size of aggregate. Because the test operation is relatively simple, and the peeling of the asphalt on the aggregate can be visually observed, it is widely used. However, this method is a qualitative evaluation, the evaluation of asphalt spalling is highly subjective, and the evaluation results vary from person to person, so the evaluation results are not accurate enough.

Therefore, at present, the more advanced surface energy method is adopted. By testing the surface energy parameters of asphalt, aggregates and fillers, the surface energy calculation method was used to obtain the cohesive binding energy of asphalt and asphalt mortar themselves and the adhesive binding energy of asphalt and aggregate. These two indexes were used to quantify the ability of asphalt mixture to resist cohesive cracking and adhesion cracking respectively. The adhesion energy index is closely related to the adhesion cracking on the asphalt-aggregate interface, which directly affects the energy conversion and distribution of the load when the asphalt mixture works, and plays a vital role in studying the initiation and propagation of multiple cracks of asphalt mixture under tension and compression modes. In addition, the adhesion energy index is also widely used to study various engineering problems such as aging, self-healing, and water damage of asphalt mixture during service. The main application method is to bring the cohesive binding energy and adhesion binding energy measured and calculated into the formula to calculate the surface energy matching index, so as to analyze the macroscopic performance of asphalt mixture. However, this index ignores the influence of filler on the cohesive energy of asphalt mortar, so the calculation method of this matching index needs to be corrected.

SUMMARY

The purpose of this disclosure is to overcome the above technical deficiencies and provide a method for calculating surface energy matching index of specific surface area of asphalt mortar-aggregate, which can solve the problem that the current water stability index of asphalt mixture does not consider the influence of filler and specific surface area on the index.

To achieve the above technical purpose, this disclosure provides a method for calculating surface energy matching index of specific surface area of asphalt mortar-aggregate, including the following steps:

S1: determining surface energy parameter of aggregate by vapor adsorption method;

S2: determining surface energy parameter of filler by improved capillary rising method;

S3: determining specific surface area of asphalt mixture aggregate by specific surface area coefficient method;

S4: using an automatic specific surface area and pore analyzer to determine the specific surface area of the filler;

S5: calculating adhesive bond energy of the asphalt mixture and adhesive bond energy under liquid condition according to the surface energy parameter of the aggregate and the surface energy parameter of the filler;

S6 calculating the surface energy matching index of asphalt mortar-aggregate based on specific surface area according to the adhesive bond energy of the asphalt mixture, the adhesive bond energy under water conditions, the specific surface area of the asphalt mixture aggregate, and the specific surface area of the filler.

This disclosure also provides a device for calculating surface energy matching index of specific surface area of asphalt mortar-aggregate, comprising:

an aggregate surface energy parameter calculation module, which determines surface energy parameter of aggregate by vapor adsorption method;

a surface energy parameter calculation module of filler, which determines surface energy parameter of filler by improved capillary rising method;

an aggregate specific surface area calculation module, which determines specific surface area of asphalt mixture aggregate by specific surface area coefficient method;

a calculation module of the specific surface area of the filler, which uses an automatic specific surface area and pore analyzer to determine the specific surface area of the filler;

an asphalt mixture adhesive bond energy and adhesive bond energy calculation module under liquid condition, which calculates adhesive bond energy of the asphalt mixture and adhesive bond energy under liquid condition according to the surface energy parameter of the aggregate and the surface energy parameter of the filler;

a surface energy matching index calculation module of asphalt mortar-aggregate based on specific surface area, which calculates the surface energy matching index of asphalt mortar-aggregate based on specific surface area according to the adhesive bond energy of the asphalt mixture, the adhesive bond energy under water conditions, the specific surface area of the asphalt mixture aggregate, and the specific surface area of the filler.

This disclosure also provides a computer device, comprising a memory, a processor and a computer program stored in the memory and executable on the processor, when the processor executes the computer program, the steps of calculating the surface energy matching index of specific surface area of asphalt mortar-aggregate are realized.

This disclosure also provides a computer-readable storage medium, wherein the computer-readable storage medium stores a computer program, when the computer program is executed by a processor, the steps of calculating the surface energy matching index of specific surface area of asphalt mortar-aggregate are realized.

The beneficial effects of this disclosure include: the water stability of asphalt mixture is improved because the influence of the surface energy matching index of the specific surface area of asphalt mortar-aggregate is considered.

BRIEF DESCRIPTION OF THE DRAWINGS

Accompanying drawings are for providing further understanding of embodiments of the disclosure. The drawings form a part of the disclosure and are for illustrating the principle of the embodiments of the disclosure along with the literal description. Apparently, the drawings in the description below are merely some embodiments of the disclosure, a person skilled in the art can obtain other drawings according to these drawings without creative efforts. In the figures.

DETAILED DESCRIPTION OF PREFERRED EMBODIMENTS

For ease of understanding, related technical terms are explained as follows.

Surface energy (represented by "$\gamma$" in this disclosure) is defined as the work done by the external environment to the system when the unit surface area of a substance is increased at constant temperature and pressure, and the unit is erg/cm². The theoretical system adopted is the GvOC theoretical system, which is the mainstream analysis system of the international surface energy theory. The system divides surface energy into polar dispersion component ($\gamma^{AB}$) and non-polar acid-base component ($\gamma^{LW}$), polar acid-base component is further divided into polar acid component ($\gamma^+$) and polar base component ($\gamma^-$), the relationship between the surface energy and each component is shown in the following equation.

$$\gamma = \gamma^{AB} + \gamma^{LW} = 2\sqrt{\gamma^+\gamma^-} + \gamma^{LW}$$

For the binding energy of the interface between the aggregate and the asphalt, that is, the adhesion binding energy, the adhesion binding energy is generated by the interaction between the polar molecules and the non-polar molecules of the two materials. The components of the adhesion binding energy can be derived from the material surface energy parameter. The cohesive bond energy of asphalt mortar can also be characterized by the adhesive bond energy of asphalt-filler.

This disclosure provides a method for calculating surface energy matching index of specific surface area of asphalt mortar-aggregate, including the following steps:

S1: determining surface energy parameter of aggregate by vapor adsorption method.

As an embodiment, according to the principle of vapor adsorption, adding aggregate with particle size of 2.36 mm-4.75 mm into the test reagent vapor with known surface energy parameters, and testing the saturated adsorption amount of aggregate vapor at each stage.

According to computer system, selecting the BET model and carrying out a series of calculations to obtain the diffusion pressure, and the surface energy parameters of the aggregate are solved by simultaneous equations. The equations are as follows:

$$2\gamma_L + \pi_e = 2(\sqrt{\gamma_a^{LW}\gamma_b^{LW}} + \sqrt{\gamma_a^+\gamma_b^-} + \sqrt{\gamma_a^-\gamma_b^+})$$

where $\pi_e$ is the diffusion pressure; $\gamma_a^{LW}$ and $\gamma_b^{LW}$ are the non-polar acid-base components of the aggregate surface energy parameter and the asphalt surface energy parameter, respectively; $\gamma_a^+$ and $\gamma_b^+$ are the polar acid components of the aggregate surface energy parameter and the asphalt surface energy parameter, respectively; $\gamma_a^-$ and $\gamma_b^-$ are the polar alkali components of the aggregate surface energy parameter and the asphalt surface energy parameter, respectively.

S2: determining surface energy parameter of filler by improved capillary rising method.

Figure 1:
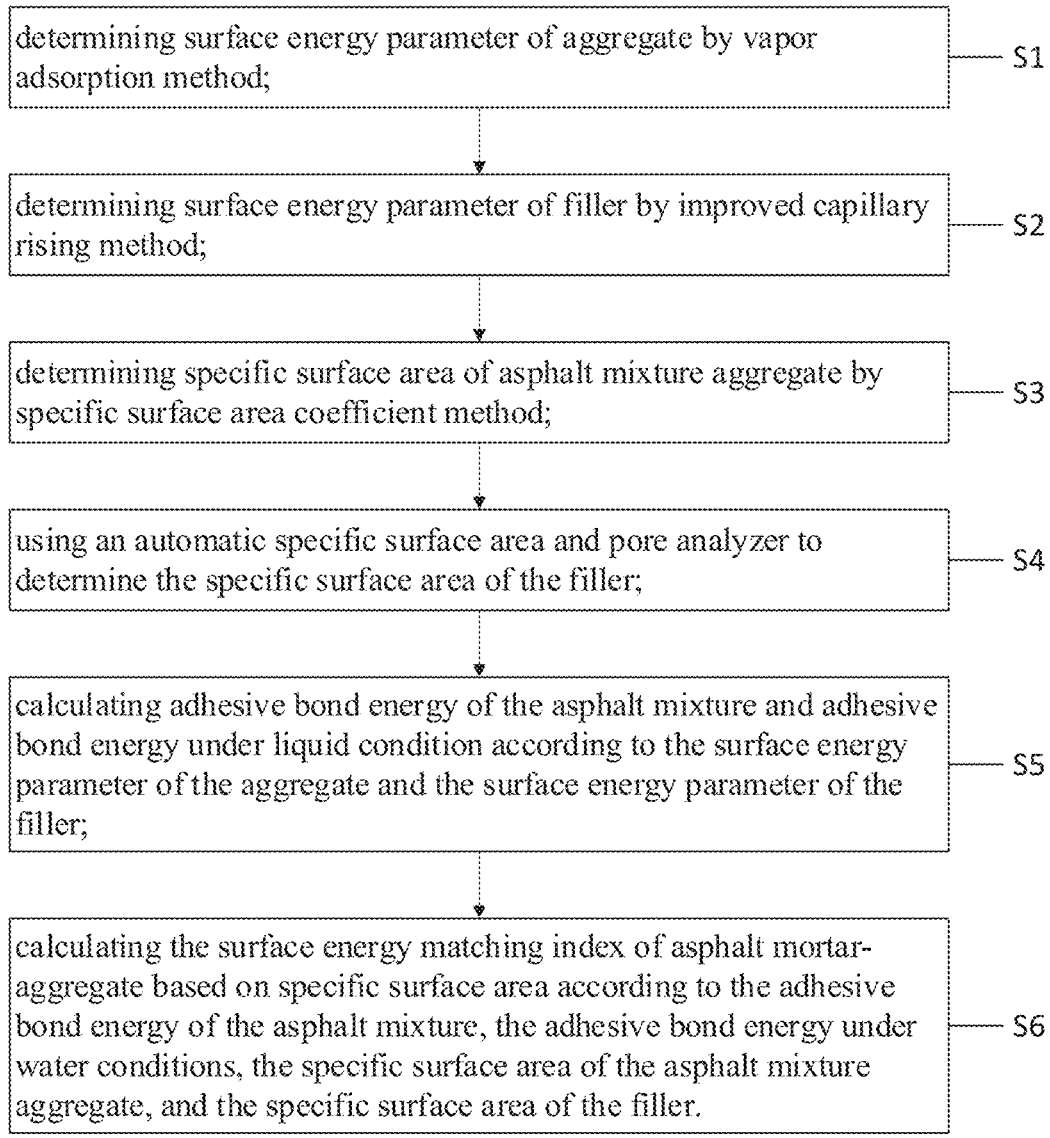
FIG. 1 is a schematic flow sheet of the method for calculating surface energy matching index of specific surface area of asphalt mortar-aggregate provided by this disclosure.
Figure 2:
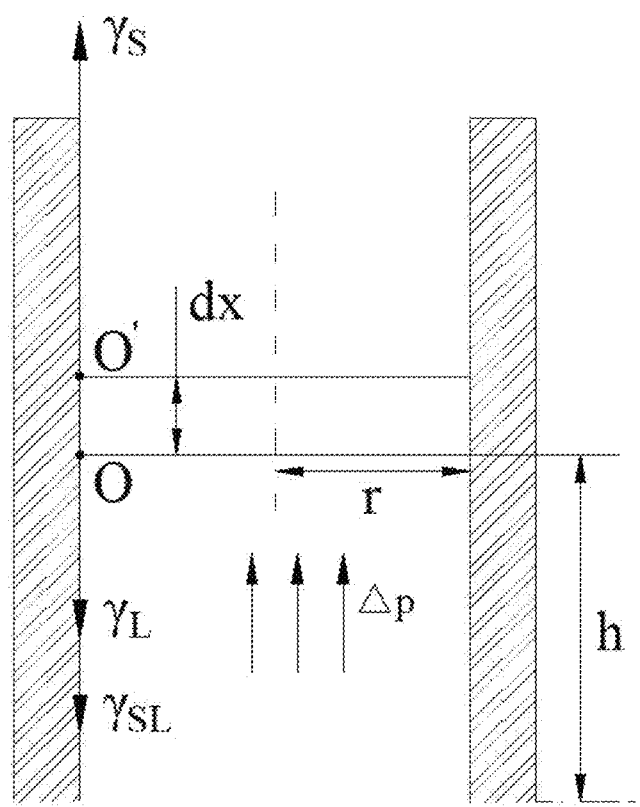
FIG. 2 is a schematic diagram of the improved capillary rising method.

Please refer to FIG. 2, FIG. 2 is a schematic diagram of the improved capillary rising method of this disclosure; as an embodiment, the disclosure proposes a method considering diffusion pressure on the basis of the traditional capillary rising method, which avoids the inaccurate test results caused by the complete wetting of the traditional test reagent and the filler without forming a stable contact angle. An automatic surface tensiometer was used for the test. Using an automatic surface tensiometer, placing the filler densely in a metal barrel and slowly adding a test reagent, calculating the effective radius of capillary and diffusion pressure of the sample to the test reagent through the curve of the change of the quality of the test reagent absorbed by the filler generated by computer, and calculating the surface energy parameter of the filler by formula (1):

$$2\gamma_L + \pi_e = 2(\sqrt{\gamma_b^{LW}\gamma_c^{LW}} + \sqrt{\gamma_b^+\gamma_c^-} + \sqrt{\gamma_b^-\gamma_c^+}) \tag{1}$$

where $\pi_e$ is the diffusion pressure; $\gamma_b^{LW}$ and $\gamma_c^{LW}$ are the non-polar acid-base components of the asphalt surface energy parameter and the filler surface energy parameter, respectively; $\gamma_b^+$ and $\gamma_c^+$ are the polar acid components of the asphalt surface energy parameter and the filler surface energy parameter, respectively; $\gamma_b^-$ and $\gamma_c^-$ are the polar alkali components of the asphalt surface energy parameter and the filler surface energy parameter, respectively.

S3: determining specific surface area of asphalt mixture aggregate by specific surface area coefficient method;

As an embodiment, according to "Technical Specification for Construction of Highway Asphalt Pavement" (JTG F40-2004), the specific surface area of asphalt mixture aggregate is determined by the method of specific surface area coefficient. First, determining the asphalt mixture gradation and the passing rate of each particle size, and then obtaining the surface area coefficient under the corresponding particle size through the aggregate surface area coefficient table, and substitute it into formula (2) to calculate the aggregate specific surface area of the asphalt mixture.

$$SSA_{aa} = \Sigma(P_i \times FA_i) \tag{2}$$

where $SSA_{aa}$ is the specific surface area of the aggregate; $P_i$ is the passing percentage of each particle size of the aggregate; $FA_i$ is the surface area coefficient of the aggregate corresponding to each particle size.

S4 using an automatic specific surface area and pore analyzer to determine the specific surface area of the filler;

As an embodiment, the main process of step S4 is to put the dried filler into an instrument, set the temperature of the environmental box to 350° C., and by feeding different types and different pressures of gas, obtaining the adsorption amount, drawing a correlation curve, and calculating the specific surface area of the filler.

S5: calculating adhesive bond energy of the asphalt mixture and adhesive bond energy under liquid condition according to the surface energy parameter of the aggregate and the surface energy parameter of the filler;

As an embodiment, the calculation formulas for the adhesive bond energy of the asphalt mixture and the adhesive bond energy under liquid condition in step S5 are as follows:

$$\Delta G_{ab}^{Adhesion} = -2\left(\sqrt{\gamma_a^{LW}\gamma_b^{LW}} + \sqrt{\gamma_a^+\gamma_b^-} + \sqrt{\gamma_a^-\gamma_b^+}\right) \tag{3}$$

$$DG_{abc}^{Adhesion} = \tag{4}$$
$$2\left(\begin{array}{l}\sqrt{\gamma_c^{LW}\gamma_c^{LW}} + \sqrt{\gamma_b^{LW}\gamma_c^{LW}} - \gamma_c^{LW} - \sqrt{\gamma_a^{LW}\gamma_b^{LW}} \\ +\sqrt{\gamma_c^+}\left(\sqrt{\gamma_a^-} + \sqrt{\gamma_b^-} - \sqrt{\gamma_c^-}\right) + \sqrt{\gamma_c^-}\left(\sqrt{\gamma_a^+} + \sqrt{\gamma_b^+} - \sqrt{\gamma_c^+}\right) \\ -\left(\sqrt{\gamma_a^+\gamma_b^-} + \sqrt{\gamma_a^-\gamma_b^+}\right)\end{array}\right)$$

where $\Delta G_{ab}^{Adhesion}$ is the adhesive bond energy between aggregate and asphalt; $\gamma_a^{LW}$ and $\gamma_b^{LW}$ are the non-polar components of the aggregate surface energy parameter and the asphalt surface energy parameter, respectively: $\gamma_a^+$ and $\gamma_b^+$ are the polar acid components of the aggregate surface energy parameter and the asphalt surface energy parameter, respectively; $\gamma_a^-$ and $\gamma_b^-$ are the polar alkali components of the aggregate surface energy parameter and the asphalt surface energy parameter, respectively; $DG_{abc}^{Adhesion}$ is the adhesion binding energy in the presence of liquid; $\gamma_c^{LW}$ is the non-polar component of the filler liquid surface energy parameter; $\gamma_c^-$ is the polar acid component of the filler liquid surface energy parameter; $\gamma_e^-$ is the polar base component of the filler liquid surface energy parameter.

S6: calculating the surface energy matching index of asphalt mortar-aggregate based on specific surface area according to the adhesive bond energy of the asphalt mixture, the adhesive bond energy under water conditions, the specific surface area of the asphalt mixture aggregate, and the specific surface area of the filler.

As an embodiment, the specific surface area-based asphalt mortar-aggregate surface energy matching index is specifically as follows:

$$ER_2 = \left|\frac{\Delta G_{ab}^{Adhesion} \times SSA_{aa} - \Delta G_a^{Cohesion} \times SSA_{af}}{\Delta G_{abc}^{Adhesion} \times SSA_{aa}}\right| \tag{5}$$

where $SSA_{af}$ is the specific surface area of the filler.

As an embodiment, according to the surface energy matching index of asphalt mortar-aggregate based on specific surface area, asphalt mixtures of different synthetic gradations were prepared, and the water-immersion Marshall test and freeze-thaw splitting test of asphalt mixture in the specification were carried out to obtain the residual stability and Freeze-thaw splitting strength ratio of two indicators. Furthermore, the water stability test results are compared with the matching index of asphalt mortar-aggregate based on specific surface area, and the accuracy of using the surface energy matching index of asphalt mortar-aggregate based on specific surface area to characterize the water stability of asphalt mixture is verified.

Embodiment

The method proposed in this embodiment firstly explores the difference between the cohesive binding energy and the adhesive binding energy of the asphalt mixture by testing the surface energy parameters of the same lithological aggregate and filler. By calculating and testing the specific surface area of aggregate and filler, a calculation method of asphalt mortar-aggregate matching index based on specific surface area is proposed, and the accuracy of the index is verified by the macroscopic water damage resistance test, which provides a theoretical basis for evaluating the water damage resistance of asphalt pavement from the perspective of material surface energy.

Aggregate and Filler Surface Energy Parameter Testing

Calculating the surface energy parameters of 6 aggregates and fillers of the same lithology and the same origin according to the test methods described in steps S1 and S2, and use formula (7) to calculate the total surface energy change rate of the aggregate and filler. The results are summarized in Table 1.

$$w = \frac{\gamma_{aa} - \gamma_{af}}{\gamma_{aa}} \times 100\% \tag{7}$$

where w is total surface energy change rate; $\gamma_{aa}$ is total surface energy of aggregate; $\gamma_{af}$ is total surface energy of filler.

TABLE 1

Surface energy parameters of filler and aggregate

| Lithology type | Material type | Surface energy parameter (ergs/cm²) | | | | | Total surface energy change rate |
|---|---|---|---|---|---|---|---|
| | | $\gamma_a^{LW}$ | $\gamma_a^+$ | $\gamma_a^-$ | $\gamma_a^{AB}$ | $\gamma_a$ | |
| Cape Mountain Rock | filler | 46.48 | 0.26 | 891.57 | 30.63 | 77.11 | 43.00% |
| | aggregate | 85.04 | 3.92 | 373.22 | 50.23 | 135.27 | |
| Diabase | filler | 45.32 | 0.26 | 416.05 | 20.92 | 66.24 | 29.33% |
| | aggregate | 81.78 | 3.25 | 208.02 | 43.56 | 93.73 | |
| Basalt | filler | 37.00 | 0.72 | 390.74 | 33.60 | 70.61 | 48.10% |
| | aggregate | 77.58 | 2.56 | 333.75 | 58.46 | 136.04 | |
| Limestone | filler | 44.75 | 0.97 | 395.62 | 39.09 | 83.84 | 43.12% |
| | aggregate | 73.74 | 2.22 | 611.75 | 73.66 | 147.40 | |
| Granite | filler | 34.29 | 0.04 | 434.75 | 8.59 | 42.88 | 54.08% |
| | aggregate | 73.45 | 0.23 | 392.39 | 19.00 | 92.45 | |

It can be seen from Table 1 that the total amount and component of surface energy of fillers and aggregates from the same lithology and the same origin are quite different. Among them, the non-polar dispersion component of aggregate surface energy and the polar acid-base component are generally larger than the non-polar dispersion component of surface energy of filler, and the total surface energy of aggregate is generally larger than that of filler. The surface energy change rate was 43.53%. The surface energy of aggregate and filler directly affects the interfacial adhesion work between asphalt and aggregate and the adhesion work inside the asphalt mortar. From this, it can be inferred that the difference in surface energy parameters between aggregate and filler is the fundamental reason for the difference between the anti-cracking performance of asphalt-aggregate and the anti-cracking performance of asphalt mortar. The next section will focus on the main reasons for the difference in surface energy parameters between aggregate and filler.

Asphalt Surface Energy Parameter Testing

Figure 3:
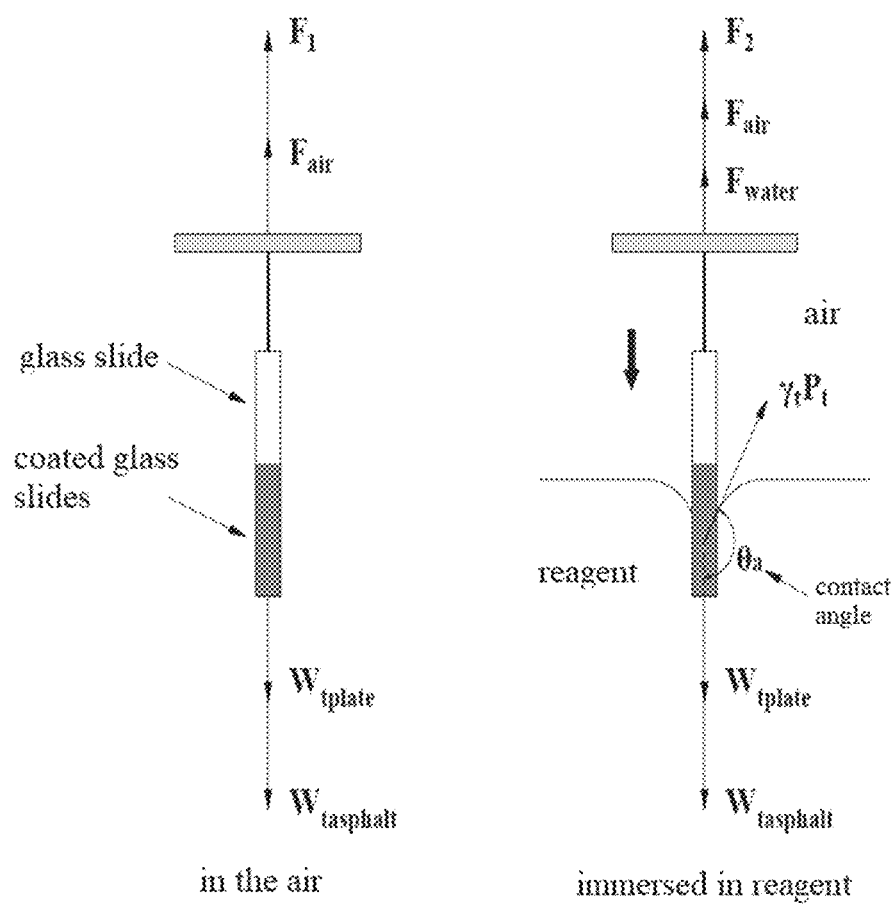
FIG. 3 is a schematic diagram of the principle of the plug-in method.

Please refer to FIG. 3, FIG. 3 is a schematic diagram of the principle of the plug-in method, the asphalt surface energy test adopts the plug-in method and adopts an automatic surface tensiometer. The force change of the prepared smooth asphalt-coated glass slide during immersion in the test reagent is recorded by computer, and the dynamic contact angle between the asphalt-coated glass slide and the test reagent is calculated according to the principle of mechanical equilibrium, and finally the asphalt surface energy parameters are calculated, and the obtained test results are shown in Table 2.

TABLE 2

| | Surface energy parameters of asphalt | | | | |
|---|---|---|---|---|---|
| | Surface energy parameter (ergs/cm²) | | | | |
| Kind of Asphalt | $\gamma_b^{LW}$ | $\gamma_b^+$ | $\gamma_b^-$ | $\gamma_b^{AB}$ | $\gamma_b$ |
| SBS (I-D) modified asphalt | 24.05 | 0.13 | 4.27 | 1.48 | 25.53 |

Comparison and Analysis of Specific Surface Area of Aggregates and Fillers

In this test, three groups of diabase AC-13C and limestone AC-20C graded asphalt mixtures were selected for the test, and according to the test methods described in steps S3 and S4, the specific surface areas of aggregates and fillers in 6 different types of asphalt mixtures were comparatively analyzed. Among them, the aggregates are diabase and limestone from the same origin as in Table 1, the asphalt is SBS (I-D) type modified asphalt, and the filler is limestone powder. The synthetic gradation table of specific gradation is shown in Table 3 and Table 4.

TABLE 3

Synthetic gradation table of three groups of diabase AC-13C gradation

| | The mass percentage that passed the following square mesh sieve (mm) | | | | | | | | | |
|---|---|---|---|---|---|---|---|---|---|---|
| mesh size | 16 | 13.2 | 9.5 | 4.75 | 2.36 | 1.18 | 0.6 | 0.3 | 0.15 | 0.075 |
| Gradation range | 100 | 90-100 | 68-85 | 38-68 | 24-50 | 15-38 | 10-28 | 7-20 | 5-15 | 4-8 |
| Synthetic grading (1# grading) | 100 | 95.9 | 79.4 | 52.3 | 27.1 | 21.0 | 15.2 | 11.3 | 8.8 | 6.6 |
| Synthetic grading (2# grading) | 100 | 96.5 | 82.3 | 56.6 | 27.1 | 20.9 | 15.1 | 11.3 | 8.8 | 6.7 |
| Synthetic grading (3# grading) | 100 | 96.4 | 81.6 | 53.5 | 28.4 | 22.1 | 15.9 | 11.8 | 9.1 | 6.9 |

TABLE 4

Synthetic gradation table of three groups of diabase AC-20C gradation

| | The mass percentage that passed the following square mesh sieve (mm) | | | | | | | | | | | |
|---|---|---|---|---|---|---|---|---|---|---|---|---|
| mesh size | 26.5 | 19 | 16 | 13.2 | 9.5 | 4.75 | 2.36 | 1.18 | 0.6 | 0.3 | 0.15 | 0.075 |
| Gradation range | 100 | 90-100 | 78-92 | 62-80 | 50-72 | 26-56 | 16-44 | 12-33 | 8-24 | 5-17 | 4-13 | 3-7 |
| synthetic grading | 100 | 97.7 | 89.1 | 77.3 | 54.8 | 36.2 | 24.4 | 19.9 | 14.5 | 10.0 | 7.4 | 5.7 |
| (1# grade) | 100 | 97.8 | 89.5 | 78.1 | 54.4 | 34.6 | 23.0 | 18.8 | 13.7 | 9.5 | 7.1 | 5.5 |
| synthetic grading | 100 | 97.7 | 89.1 | 77.2 | 52.8 | 36.5 | 25.7 | 20.9 | 15.2 | 10.4 | 7.7 | 5.8 |

Determining the specific surface area of the aggregate according to the surface area coefficient method, and use the direct test method to test the specific surface area of the filler. The calculation results are summarized in Table 5 and Table 6.

TABLE 5

Aggregate specific surface area

| Gradation type | | Specific surface area ($m^2 \cdot kg^{-1}$) |
|---|---|---|
| Diabase AC-13C | Synthetic grading (1# grading) | 5.15545 |
| | Synthetic grading (2# grading) | 5.20134 |
| | Synthetic grading (3# grading) | 5.37504 |
| Limestone AC-20C | Synthetic grading (1# grading) | 4.88293 |
| | Synthetic grading (2# grading) | 4.69119 |
| | Synthetic grading (3# grading) | 5.02551 |

TABLE 6

Filler specific surface area

| Filler Type | Specific surface area ($m^2 \cdot kg^{-1}$) |
|---|---|
| limestone powder | 5.6465 |

Asphalt Mortar-Aggregate Matching Index Based on Specific Surface Area

The adhesion bond energy between asphalt and aggregate reflects the adhesion performance between the two. The higher the adhesion bond energy, the better the adhesion performance between the two. The adhesive bond energy between asphalt-aggregate-water three-phase materials reflects the degree of spalling of asphalt mixture under the action of water. Therefore, considering the above factors and other factors comprehensively, formula (8) is used to calculate the index to evaluate the water stability of the asphalt mixture.

$$ER_1 = \left| \frac{\Delta G_{ab}^{Adhesion} - G_a^{Cohension}}{\Delta G_{abc}^{Adhesion}} \right| \quad (8)$$

where $ER_1$ is an index for evaluating the water stability of asphalt mixture, the larger the value, the better the water stability; $G_a^{Cohesion}$ is the cohesive binding energy of asphalt.

However, this evaluation index does not consider the influence of filler and specific surface area on this index, so this disclosure proposes an asphalt mortar-aggregate matching index based on specific surface area. Firstly, the surface energy parameters of asphalt, aggregates, and fillers obtained from test are brought into equations (2) and (3) to calculate the cohesive bond energy, adhesive bond energy, and adhesive bond energy of the asphalt mixture under water condition, and then bring them into formula (5) together with the specific surface area of the material calculated by the test, and calculate the asphalt mortar-aggregate matching index based on specific surface area. The calculation results are summarized in Table 7.

TABLE 7

Calculation results of matching index

| Gradation type | | $ER_2$ value | $ER_1$ value |
|---|---|---|---|
| Diabase AC-13C | Synthetic grading (1# grading) | 0.21842 | 0.33882 |
| | Synthetic grading (2# grading) | 0.23064 | |
| | Synthetic grading (3# grading) | 0.27498 | |
| Limestone AC-20C | Synthetic grading (1# grading) | 0.16627 | 0.14978 |
| | Synthetic grading (2# grading) | 0.10653 | |
| | Synthetic grading (3# grading) | 0.20774 | |

It can be seen from the calculation results that there is a certain difference between the improved $ER_2$ value and the original $ER_2$ value, and the maximum difference between the improved $ER_2$ value and the original $ER_2$ value is 35.53%, indicating that the specific surface area of aggregate and filler greatly affects the calculation results of the matching index. Hence this method further improves the accuracy of the indicator. The order of the x value in the AC-13C gradation is 3 #>2 #>1 #; the order of the $ER_2$ value in the AC-20C gradation is 3 #>1 #>2 #. It can be seen from the calculation that the $ER_2$ value of the third synthetic gradation of AC-13C and AC-20C is the largest, indicating that its water stability performance is the best. On the contrary, the first synthetic gradation of AC-13C and the second synthetic gradation of AC-20C have the smallest $ER_2$ value and the worst water stability performance. From this, it can be inferred that the higher the content of fine aggregate in the three gradations, the higher the value of $ER_2$, which indicates that the content of fine aggregate can be appropriately increased in the design process of the mix ratio of the asphalt mixture to improve the water stability of asphalt mixture.

Test Verification of Water Stability of Asphalt Mixture

In order to macroscopically evaluate the water stability performance of asphalt mixture with different synthetic gradations, the immersion Marshall test and freeze-thaw splitting test of asphalt mixture commonly used in engineering in China are adopted, and the test is carried out according to the current specification of China. Two indexes of immersion residual stability and freeze-thaw splitting strength ratio are obtained. The average value is obtained through multiple tests, and the test results are shown in FIG. 4.

Figure 4:
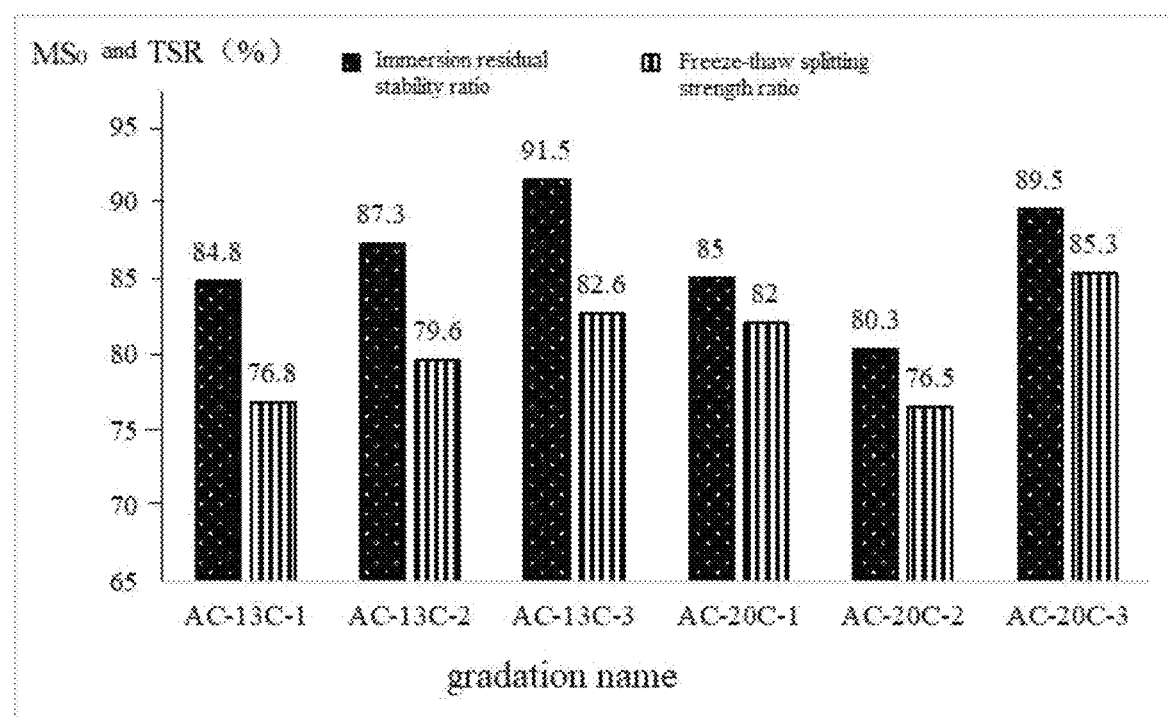
FIG. 4 is the schematic diagram of the water stability test result of the asphalt mixture in an embodiment of this disclosure.

As can be seen from FIG. 4, for AC-13C gradation, the order of water stability index is 3 #>2 #>1 #. Among them, the third synthetic gradation has the largest immersion residual stability ratio and freeze-thaw splitting strength ratio, which are 91.47% and 82.57% respectively, reaching 85% and 80% of the specification requirements, indicating that the water stability of this gradation asphalt mixture is the best. Similarly, for AC-20C gradation, the order of water stability index is 3 #>1 #>2 #. The ratio of immersion residual stability and freeze-thaw splitting strength of the third synthetic gradation are the largest, which are 89.5% and 85.3%, respectively, indicating that the water stability of this gradation asphalt mixture is the best.

The water stability test results are compared with the asphalt mortar-aggregate matching index based on specific surface area, and it is found that the two are consistent, indicating that the asphalt mortar-aggregate surface energy matching index based on specific surface area can well characterize the water stability of asphalt mixture, which has certain theoretical and engineering practical value.

This disclosure also provides a device for calculating surface energy matching index of specific surface area of asphalt mortar-aggregate, which corresponds to the method for calculating surface energy matching index of specific surface area of asphalt mortar-aggregate, the device for calculating surface energy matching index of specific surface area of asphalt mortar-aggregate comprises:

an aggregate surface energy parameter calculation module, which determines surface energy parameter of aggregate by vapor adsorption method;

a surface energy parameter calculation module of filler, which determines surface energy parameter of filler by improved capillary rising method;

an aggregate specific surface area calculation module, which determines specific surface area of asphalt mixture aggregate by specific surface area coefficient method;

a calculation module of the specific surface area of the filler, which uses an automatic specific surface area and pore analyzer to determine the specific surface area of the filler;

an asphalt mixture adhesive bond energy and adhesive bond energy calculation module under liquid condition, which calculates adhesive bond energy of the asphalt mixture and adhesive bond energy under liquid condition according to the surface energy parameter of the aggregate and the surface energy parameter of the filler;

a surface energy matching index calculation module of asphalt mortar-aggregate based on specific surface area, which calculates the surface energy matching index of asphalt mortar-aggregate based on specific surface area according to the adhesive bond energy of the asphalt mixture, the adhesive bond energy under water conditions, the specific surface area of the asphalt mixture aggregate, and the specific surface area of the filler.

This disclosure also provides a computer device, comprising a memory, a processor and a computer program stored in the memory and executable on the processor, when the processor executes the computer program, the steps of calculating the surface energy matching index of specific surface area of asphalt mortar-aggregate are realized.

This disclosure also provides a computer-readable storage medium, wherein the computer-readable storage medium stores a computer program, when the computer program is executed by a processor, the steps of calculating the surface energy matching index of specific surface area of asphalt mortar-aggregate are realized.

The beneficial effects of this disclosure include: the water stability of asphalt mixture is improved because the influence of the surface energy matching index of the specific surface area of asphalt mortar-aggregate is considered.

It is to be understood, however, that even though numerous characteristics and advantages of this disclosure have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A method for calculating surface energy matching index of specific surface area of asphalt mortar-aggregate, including the following steps:

S1: determining surface energy parameter of aggregate by vapor adsorption method;

S2: determining surface energy parameter of filler by improved capillary rising method;

S3: determining specific surface area of asphalt mixture aggregate by specific surface area coefficient method;

S4: using an automatic specific surface area and pore analyzer to determine the specific surface area of the filler;

S5: calculating adhesive bond energy of the asphalt mixture and adhesive bond energy under liquid condition according to the surface energy parameter of the aggregate and the surface energy parameter of the filler;

S6: calculating the surface energy matching index of asphalt mortar-aggregate based on specific surface area according to the adhesive bond energy of the asphalt mixture, the adhesive bond energy under water conditions, the specific surface area of the asphalt mixture aggregate, and the specific surface area of the filler.

2. The method for calculating surface energy matching index of specific surface area of asphalt mortar-aggregate according to claim 1, wherein the improved capillary rising method in step S2 is:

using an automatic surface tensiometer, placing the filler densely in a metal barrel and slowly adding a test reagent, calculating the effective radius of capillary and diffusion pressure of the sample to the test reagent through the curve of the change of the quality of the test reagent absorbed by the filler generated by computer, and calculating the surface energy parameter of the filler by formula (1):

$$\Delta G_{ab}^{Adhesion} = -2\left(\sqrt{\gamma_a^{LW}\gamma_b^{LW}} + \sqrt{\gamma_a^+\gamma_b^-} + \sqrt{\gamma_a^-\gamma_b^+}\right) \quad (3)$$

$$DG_{abc}^{Adhesion} = 2\left(\begin{array}{c}\sqrt{\gamma_c^{LW}\gamma_c^{LW}} + \sqrt{\gamma_b^{LW}\gamma_c^{LW}} - \gamma_c^{LW} - \sqrt{\gamma_a^{LW}\gamma_b^{LW}} \\ +\sqrt{\gamma_c^+}\left(\sqrt{\gamma_a^-} + \sqrt{\gamma_b^-} - \sqrt{\gamma_c^-}\right) + \sqrt{\gamma_c^-}\left(\sqrt{\gamma_a^+} + \sqrt{\gamma_b^+} - \sqrt{\gamma_c^+}\right) \\ -\left(\sqrt{\gamma_a^+\gamma_b^-} + \sqrt{\gamma_a^-\gamma_b^+}\right)\end{array}\right) \quad (4)$$

where $\pi_e$ is the diffusion pressure; $\gamma_b^{LW}$ and $\gamma_c^{LW}$ are the non-polar acid-base components of the asphalt surface energy parameter and the filler surface energy parameter, respectively; $\gamma_b^+$ and $\gamma_c^-$ are the polar acid components of the asphalt surface energy parameter and the filler surface energy parameter, respectively; $y_b^-$ and $\gamma_c^-$ are the polar alkali components of the asphalt surface energy parameter and the filler surface energy parameter, respectively.

3. The method for calculating surface energy matching index of specific surface area of asphalt mortar-aggregate according to claim 1, wherein calculation formula of the specific surface area of asphalt mixture aggregate in step S3 is:

$$SSA_{aa} = \sum(P_i \times FA_i) \quad (2)$$

where $SSA_{aa}$ is the specific surface area of the aggregate; $P_i$ is the passing percentage of each particle size of the aggregate; $FA_i$ is the surface area coefficient of the aggregate corresponding to each particle size.

4. The method for calculating surface energy matching index of specific surface area of asphalt mortar-aggregate according to claim 3, wherein the calculation formulas for the adhesive bond energy of the asphalt mixture and the adhesive bond energy under liquid condition in step S5 are as follows:

$$2\gamma_L + \pi_e = 2\left(\sqrt{\gamma_b^{LW}\gamma_c^{LW}} + \sqrt{\gamma_b^{+}\gamma_c^{-}} + \sqrt{\gamma_b^{-}\gamma_c^{+}}\right) \quad (1)$$

where: $\Delta G_{ab}^{Adhesion}$ is the adhesive bond energy between aggregate and asphalt; $\gamma_a^{LW}$ and $\gamma_b^{LW}$ are the non-polar components of the aggregate surface energy parameter and the asphalt surface energy parameter, respectively; $\gamma_a^{+}$ and $\gamma_b^{+}$ are the polar acid components of the aggregate surface energy parameter and the asphalt surface energy parameter, respectively; $\gamma_a^{-}$ and $\gamma_b^{-}$ are the polar alkali components of the aggregate surface energy parameter and the asphalt surface energy parameter, respectively; $DG_{abc}^{Adhesion}$ is the adhesion binding energy in the presence of liquid; $\gamma_c^{LW}$ is the non-polar component of the filler liquid surface energy parameter; $\gamma_c^{+}$ is the polar acid component of the filler liquid surface energy parameter; $\gamma_c^{-}$ is the polar base component of the filler liquid surface energy parameter.

5. The method for calculating surface energy matching index of specific surface area of asphalt mortar-aggregate according to claim 4, wherein the specific surface area-based asphalt mortar-aggregate surface energy matching index is specifically as follows:

$$ER_2 = \left|\frac{\Delta G_{ab}^{Adhesion} \times SSA_{aa} - \Delta G_{a}^{Cohesion} \times SSA_{af}}{\Delta G_{abc}^{Adhesion} \times SSA_{aa}}\right| \quad (5)$$

where $SSA_{af}$ is the specific surface area of the filler.

6. A device for calculating surface energy matching index of specific surface area of asphalt mortar-aggregate, comprising:

an aggregate surface energy parameter calculation module, which determines surface energy parameter of aggregate by vapor adsorption method;

a surface energy parameter calculation module of filler, which determines surface energy parameter of filler by improved capillary rising method;

an aggregate specific surface area calculation module, which determines specific surface area of asphalt mixture aggregate by specific surface area coefficient method;

a calculation module of the specific surface area of the filler, which uses an automatic specific surface area and pore analyzer to determine the specific surface area of the filler;

an asphalt mixture adhesive bond energy and adhesive bond energy calculation module under liquid condition, which calculates adhesive bond energy of the asphalt mixture and adhesive bond energy under liquid condition according to the surface energy parameter of the aggregate and the surface energy parameter of the filler;

a surface energy matching index calculation module of asphalt mortar-aggregate based on specific surface area, which calculates the surface energy matching index of asphalt mortar-aggregate based on specific surface area according to the adhesive bond energy of the asphalt mixture, the adhesive bond energy under water conditions, the specific surface area of the asphalt mixture aggregate, and the specific surface area of the filler.

7. A computer device, comprising a memory, a processor and a computer program stored in the memory and executable on the processor, when the processor executes the computer program, the steps of calculating the surface energy matching index of specific surface area of asphalt mortar-aggregate according to claim 1 are realized.

8. A non-transitory computer-readable storage medium, wherein the non-transitory computer-readable storage medium stores a computer program, when the computer program is executed by a processor, the steps of calculating the surface energy matching index of specific surface area of asphalt mortar-aggregate according to claim 1 are realized.

* * * * *